(12) United States Patent
Liu et al.

(10) Patent No.: US 7,293,450 B2
(45) Date of Patent: Nov. 13, 2007

(54) OIL QUALITY SENSOR STRUCTURE FOR PERMANENT APPLICATIONS

(75) Inventors: James Z T Liu, Hudson, NH (US); Aziz Rahman, Sharon, MA (US); Michael L. Rhodes, Richfield, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/244,594

(22) Filed: Oct. 5, 2005

(65) Prior Publication Data
US 2007/0074562 A1   Apr. 5, 2007

(51) Int. Cl.
*G01N 11/00* (2006.01)
(52) U.S. Cl. .................... 73/53.05; 73/54.01
(58) Field of Classification Search .............. 73/53.05, 73/54.41, 54.01, 54.02, 53.07, 64.53
See application file for complete search history.

(56) References Cited

U.S. PATENT DOCUMENTS

| 3,253,219 | A |   | 5/1966 | Littler |   |
|---|---|---|---|---|---|
| 3,881,805 | A | * | 5/1975 | Larson, III | 359/308 |
| 4,691,714 | A |   | 9/1987 | Wong et al. | 128/738 |
| 4,782,332 | A |   | 11/1988 | Cipris et al. | 340/603 |
| 4,792,791 | A |   | 12/1988 | Cipris et al. | 340/603 |
| 5,235,235 | A |   | 8/1993 | Martin et al. | 310/313 D |
| 5,274,335 | A |   | 12/1993 | Wang et al. | 324/689 |
| 5,301,643 | A |   | 4/1994 | Garcyalny | 123/198 D |
| 5,336,396 | A |   | 8/1994 | Shetley | 210/90 |
| 5,869,763 | A |   | 2/1999 | Vig et al. | 73/580 |
| 5,878,708 | A |   | 3/1999 | Ruman | 123/196 M |
| 6,044,332 | A |   | 3/2000 | Korsah et al. | 702/76 |
| 6,076,406 | A |   | 6/2000 | Blair et al. | 73/590 |
| 6,293,136 | B1 |   | 9/2001 | Kim | 73/19.03 |
| 6,508,100 | B2 |   | 1/2003 | Berndorfer | 73/1.02 |
| 6,553,812 | B2 | * | 4/2003 | Park et al. | 73/54.01 |
| 6,557,396 | B2 |   | 5/2003 | Ismail et al. | 73/53.05 |

(Continued)

FOREIGN PATENT DOCUMENTS

DE   10345253 A1   5/2005

(Continued)

OTHER PUBLICATIONS

Jakoby et al., "The potential of Microacoustic SAW and BAW Based Sensors for Automotive Applications—A Review," IEEE Sensors Journal, vol. 2, No. 5, Oct. 2002.*

(Continued)

*Primary Examiner*—Hezron Williams
*Assistant Examiner*—Jacques M. Saint-Surin
(74) *Attorney, Agent, or Firm*—Kermit D. Lopez; Luis M. Ortiz; Matthew F. Lambrinos

(57) ABSTRACT

An oil quality sensor system comprise an acoustic wave viscosity and an etch rate sensor. The etch rate sensor system includes a piezoelectric substrate and one or more sensing layers configured upon the piezoelectric substrate. A layer of gold is generally configured above the sensing layer(s), such that the gold layer provides protection to the sensing layer(s), thereby extending the operating life of the resulting etch rate sensor system. The sensing layer(s) generally comprises one or more reactive electrodes. The etch rate sensor system can be adapted for use in a permanent oil quality sensor application.

18 Claims, 1 Drawing Sheet

U.S. PATENT DOCUMENTS

| | | | |
|---|---|---|---|
| 6,776,024 B2 | 8/2004 | Jakoby | 73/10 |
| 6,786,080 B2 | 9/2004 | Jakoby et al. | 73/54.01 |
| 6,799,458 B2 | 10/2004 | Ismail et al. | 73/304 C |
| 2004/0035398 A1 | 2/2004 | Klugl et al. | 123/456 |
| 2004/0255648 A1* | 12/2004 | Sparks | 73/54.41 |
| 2006/0033189 A1* | 2/2006 | Haba et al. | 257/678 |
| 2007/0068256 A1* | 3/2007 | Xu et al. | 73/597 |

FOREIGN PATENT DOCUMENTS

WO    WO 91/17423 A    11/1991

OTHER PUBLICATIONS

Hammond J M et al., An Acoustic Automotive Engine Oil Quality Sensor, Frequency Control Symposium, IEEE, NY, USA, May 1997, pp. 72-80.

* cited by examiner

OIL QUALITY SENSOR STRUCTURE FOR PERMANENT APPLICATIONS

TECHNICAL FIELD

Embodiments are generally related to sensing devices. Embodiments are also related to oil quality sensors. Embodiments are additionally related to acoustic wave sensors, such as, for example, Surface Acoustic Wave (SAW) and Bulk Acoustic Wave (BAW) sensor devices.

BACKGROUND

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for sensor applications, such as in chemical vapor detection. Acoustic wave sensors are so named because they use a mechanical, or acoustic, wave as the sensing mechanism. As the acoustic wave propagates through or on the surface of the material, any changes to the characteristics of the propagation path affect the velocity, phase, and/or amplitude of the wave.

Changes in acoustic wave characteristics can be monitored by measuring the frequency, amplitude, or phase characteristics of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the SAW sensor. Examples of acoustic wave sensors include acoustic wave detection devices, which are utilized to detect the presence of substances, such as chemicals, or environmental conditions such as temperature and pressure.

An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave (SAW/SH-SAW) and amplitude plate mode (APM/SH-APM) devices are typically fabricated using photolithographic techniques with comblike interdigital transducers (IDTs) placed on a piezoelectric material. Surface acoustic wave devices may have a delay line, a filter or a resonator configuration. Bulk acoustic wave devices are typically fabricated using a vacuum plater, such as those made by CHA, Transat or Saunder. The choice of the electrode materials and the thickness of the electrode are controlled by filament temperature and total heating time. The size and shape of electrodes are defined by proper use of mask. Based on the foregoing, it can be appreciated that acoustic wave devices, such as a surface acoustic wave resonator (SAW-R), surface acoustic wave filter (SAW-filter), surface acoustic wave delay line (SAW-DL), surface transverse wave (STW), bulk acoustic wave (BAW), can be utilized in various sensing measurement applications.

One promising application for micro-sensors involves oil filter and oil quality monitoring. Except under very unusual circumstances, oil does not "wear out", "break down" or otherwise deteriorate to such an extent that it needs to be replaced. What happens is that it becomes contaminated with water, acids, burnt and un-burnt fuel, carbon particles and sludge so that it can no longer provide the desired degree of protection for engine components. Most oil filters in modern vehicles do not remove all the contaminants. A filter can only remove solid particles above a certain size. It cannot remove water, acids, or fuel dilution, all of which pass through the full-flow filter just as readily as the oil.

Motor oils are fortified with inhibitors that provide a remarkable stability and resistance to oxidation and deterioration. Such inhibitors also contain acid neutralizing additives that can eliminate acidity or engine corrosion. There is a limit, however, to the amount of contamination that even the best oil can neutralize, and there comes a time when the only satisfactory procedure is to drain the oil and replenish the engine with a new charge. Thus there arises the necessity for regular oil changes.

The question is now "How often should engine oil be changed?" Unfortunately there is no simple answer to this. From what we have already discussed, it will now be apparent that we change oil, not because it has deteriorated, but because it has become contaminated with various harmful substances, and the greater the rate at which these enter the oil, the sooner an oil change will be necessary.

The things that influence this include engine condition and method of operation. A vehicle that is used mainly for short distance stop-start running will require more frequent oil changes than one used for regular long distance traveling, and a worn engine with leaky piston rings will contaminate the oil quicker than a new engine in good mechanical condition.

It should also be in mind that a high performance product (more additives) can handle more contaminate than other products, and hence longer oil change periods can be justified. As a final comment on this subject, it is worth mentioning that it is normal for oil to darken in service. This is not an indication that the oil has deteriorated. It shows that it is picking up its load of contaminates and keeping then in suspension, where they can do no harm, and where they can be removed from the engine when the oil is changed.

Motor oil must perform two primary functions. It must lubricate the engine and it also has to serve as a collector of contamination. The contamination comes from the engine combustion chambers where the gasoline is burned to produce powder. There are two different types of fuel combustion in engines: efficient combustion or clean burning; and inefficient combustion or dirty burning.

When dirty combustion occurs in engines, soot isn't the only thing formed. Sticky, gummy products, which oil chemists call resins, and lead oxyhalides. Small quantities of acidic combustion products are also formed. Last, but by no means least, is water. For every gallon of gasoline burned, a little over one gallon of water may be formed, believe it or not! So during the burning of gasoline in engines, we have a potential problem with soot, resins, acids, and water which are formed. If these combustion products work down past the pistons to get into the crankcase oil, then we do have the problem of dirty, contaminated oil. If the oil is allowed to become too dirty and contaminated, sludge deposits will form to cause plugged piston rings, oil pump screens and oil filters. Engine wear and even engine damage can then result.

When engine is cold, the dirty combustion occurs, and the contamination work down past the pistons and get into the oil. An engine used in typical city driving with a lot of short runs, stopping and starting, seldom gets a chance to warm up thoroughly and operates at its lowest efficiency, which means dirty combustion. The cold cylinder walls of the engine act as condensers for the soot, resins, water and unburned gasoline. These are washed down past the pistons into the crankcase oil. An engine has to have a good, steady run before it is thoroughly warmed up, and a considerable longer time in winter. The first few minutes after each cold engine starts is the hardest on the oil.

After an engine has been run long enough to get thoroughly warmed up, it's then operating at its best efficiency, which means clean combustion and a minimum of combustion soot and contaminates. Furthermore, the hot cylinder walls no longer act as condensers, so the contaminates are minimized and don't work down past the pistons into the crankcase oil.

A truck, bus or passenger car driven at highway speed on a length trip is an example of perhaps the easiest job to lubricate and the least demanding on an oil of good quality. The really tough lubricating job is the engine, which experiences only short runs with lots of stops and starts, especially in cold weather. The worst conditions for both the engine and the oil are the very conditions under which the great majority of passenger cars are used most of the time.

Diesel engines are particularly hard on oil because of oxidation from acidic combustion. As the oil wears, it oxidizes and undergoes a slow build-up of total acids number (TAN). A pH sensor is capable of direct measurement of TAN and an indirect measurement of total base number (TBN), providing an early warning of oil degradation due to oxidation and excess of water. The acids and water build-up is also related to the viscosity of the oil.

Knowing the condition of oil in the field would obviously be extremely beneficial information to truck fleet maintenance managers and maintenance personnel. A permanently installed oil quality sensor system can deliver the above information.

Currently, fleets that perform analysis on their lubes utilize complete laboratory oil analysis. Primarily due to the cost of laboratory analysis, these tests are only performed on a routine basis, i.e. monthly or at each oil drain interval. Laboratory oil analysis serves two basic functions. The first function is to monitor the condition of the lube oil. Lube oil within a health engine degrades at a slow rate with normal use. Therefore, lab analysis can give us forewarning and allows us to schedule routine oil drains. Complete lab analysis is very effective in accomplishing this goal and first function.

However, it is at the second function where lab analysis falls a little short and that is giving sufficient warning as to failures such as, coolant leaks and stress related metal failures. We normally sample our equipment on a monthly basis and while this is a sufficient interval to safely monitor the lube condition, many times this frequency is not sufficient in detecting engine problems. After all, analysis is used to detect the "Problem" before "Failure" and "Downtime" can occur.

An example of this situation is as follows: A company samples their equipment on a monthly basis. On the first day of the month a sample of the used oil is taken and sent to the lab for analysis. On the second day, unknown to the maintenance personnel and the oil lab, a coolant leak develops within the engine. The next-scheduled time for another complete laboratory analysis sample to be taken is twenty-nine days away. Within the next several days, the coolant leak degrades the oil within the engine to the point that it causes wear to occur to bearings and other parts of the engine.

Somewhere between the seventh and the tenth day the operator receives the results from the lab sample taken on the first day of the month. These results were taken before the problem occurred and shows no problems within the engine and that the oil is suitable for further use. Two days after receiving this report, the operator notices that the oil is becoming cloudy and that the engine is making a little steam. The routine monthly sampling of the used oil was not effective in achieving its goal.

The need is immense for a permanently installed sensor device that can determine the condition of the lube and equipment which can be used on a more frequent basis than complete laboratory analysis sampling. This need can be met by the use of the disclosure here.

The permanently installed oil sensor could be used on oil within many different types of equipment such as, gasoline engines, diesel engines, natural gas engines, hydraulic systems, transmissions, compressors, turbines, and more. With monthly laboratory analysis, one only has 12 chances a year to catch a problem. Using the permanently installed oil sensor system on a real time basis, one can increase their chances of detecting an engine oil problem.

The permanently installed oil sensor system will prove to be an effective method of monitoring and determining the condition of both lube and equipment. The sensor system monitors the total amount of contamination present within the lube oil by measuring the viscosity and TAN of the oil. Although complete laboratory analysis delivers a more detailed analysis of the oil, this sensor unit is highly efficient in determining whether the oil and equipment is in normal operating condition. When a problem with the equipment occurs, the unit easily detects this problem by detecting the elevated TAN and viscosity of the oil due to the excess amount of contamination present within the lube oil. The permanently installed oil sensor system will be used as a simple monitoring tool to let the driver or maintenance personnel know whether the equipment is within a "Normal" or "Abnormal" operating condition.

Low temperature start-ability, fuel economy, thinning or thickening effects at high and/or low temperatures, along with lubricity and oil film thickness in running automotive engines are all dependent upon viscosity. Frequency changes in viscosity have been utilized in conventional oil detection systems. The frequency changes caused by small changes in viscosity of highly viscous liquids, however, are very small. Because of the highly viscous loading, the signal from a sensor oscillator is very "noisy" and the accuracy of such measurement systems is very poor. Moreover, such oscillators may cease oscillation due to the loss of the inductive properties of the resonator.

TAN is a property typically associated with industrial oils. It is defined as the amount of acid and acid-like material in the oil. Oxidation and nitration resins make up the majority of this material. As the oil is used, acidic components build up in the lubricant causing the TAN number to increase. A high TAN number represents the potential for accelerated rust, corrosion and oxidation and is a signal that the oil should be replaced. Critical TAN numbers are dependant on oil type.

There is a need to provide a sensor system which can be utilized to monitor, in a sensitive manner, the etching effects of etchants, such as acids contained in oils. There is also a need to provide a sensor system which can monitor corrosion or degradation of engines or other devices caused by exposure to such etchants. It is believed that acoustic wave sensors may well be suited for such monitoring as indicated by the embodiments described herein.

One of the problems with acoustic wave devices utilized in oil monitoring applications is that such devices are susceptible to attack by acids and other analytes present in the oil. When an etch rate sensor, for example, utilized oil monitoring applications is exposed to oil and/or acids, the acids tend to attack the sensor electrodes, thereby reducing the life of the sensor. It is believed that an improved etch rate sensor design and configuration is required to overcome these problems. Such a device is described in greater detail herein.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved sensing devices and applications.

It is another aspect of the present invention to provide for an improved etch rate sensor system.

It is yet a further aspect of the present invention to provide for an improved acoustic wave sensor system.

The aforementioned aspects of the invention and other objectives and advantages can now be achieved as described herein. An etch rate sensor system includes a piezoelectric substrate and one or more sensing layers configured upon the piezoelectric substrate. A layer of gold is generally configured above the sensing layer(s), such that the gold layer provides protection to the sensing layer(s), thereby extending the operating life of the resulting etch rate sensor system. The sensing layer(s) generally comprises one or more reactive electrodes. The etch rate sensor system can be adapted for use in a permanent filter application.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
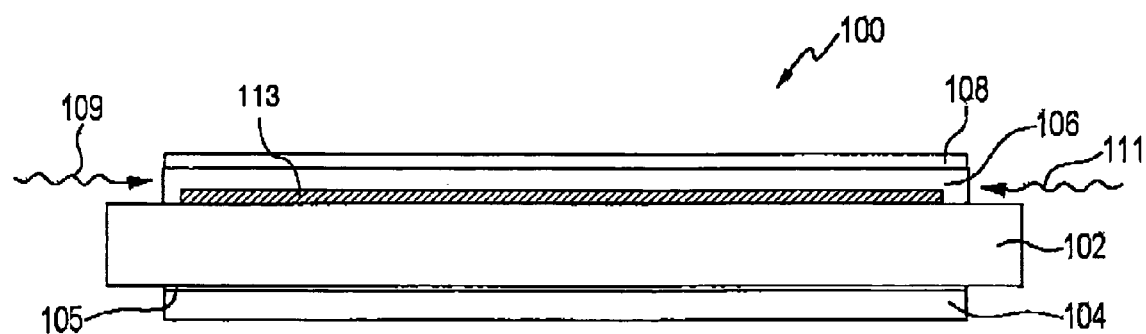
FIG. 1 illustrates a side view of an etch rate sensor system that can be implemented in accordance with a preferred embodiment.

FIG. 1 illustrates a side view of an etch rate sensor system 100 that can be implemented in accordance with a preferred embodiment. The etch rate sensor system 100 is designed in order to provide for an extended sensor life. When an etch rate sensor is exposed to material such oil and/or acids, the acids and/or oil material attack the sensor electrodes. If the reactive electrodes are covered with gold, however, exposure to the oil and/or acids is limited, forcing the acids to react only through areas exposed under the gold cover. The thickness to be etched (i.e., or the sensor life) can therefore be extended significantly. The thickness of the electrode can be, for example, approximately 4000 Angstroms, while the electrode size can be in a range of approximately 4 mm to 6 mm. In this manner, the effective thickness (i.e., the thickness to be etched or the sensor life) can be increased 5000 to 10000 times.

The etch rate sensor system 100 generally includes a substrate 102, which may be formed from, for example, a piezoelectric material. One or more sensing layers 104 and 106 can be formed on the substrate 102. Layer 104 can be formed, for example on the top side of substrate 102, while layer 106 can be configured on the bottom side of substrate 102. A layer 108 can then be formed on the sensing layer 106. Note that the sensing layer 106 can be configured in the form of one or more reactive electrodes.

When a reactive electrode of sensing layer 106 is exposed directly to acids and/or oil, the reactive oil may be etched away by the adds from the top and bottom sides of the substrate 102. Thus, the operating life of the etch rate sensor system 100 can be determined by the thickness of the electrode(s) and associated sensing layers 104, 106. When the top of the reactive electrode or sensing layer 106 is covered by the gold layer 108, however, the acids are forced instead to attack the reactive electrode from the "side" as indicated by the curved arrows 109 and 111 depicted in FIG. 1. In this case, the "effective thickness" of the electrode or sensing layer 106 is equal to half the width/length of the electrode or sensing layer 106, thereby significantly extending the life of the etch rate sensor system 100. Note that a sacrificial layer 113 can be located between the piezoelectric substrate 102 and said gold layer 108 depicted in FIG. 1 in order permit a reaction to occur from a radial direction thereof.

In the example illustrated in FIG. 1, the gold layer 108 can possess a thickness of, for example 100 to 1500 Angstroms, while the sensing layer 106 may possess a thickness in range of, for example, 2000-4000 Angstroms. Gold layer 108 is therefore configured above the sensing layer 106 in order to provide protection to the sensing layer 106, thereby extending the life of the system 100, which can function as an oil quality sensing system. Note that sensing layers 106 and/or 104 together or individually can function as acoustic wave viscosity sensing components, while an etch rate sensing component or device can be formed from the piezoelectric substrate 102 and one or more of sensing layers 104, 106 configured upon said piezoelectric substrate 102.

The sensing layers 104, 106 can be formed from materials such as Fe, Ni, or Cr. The piezoelectric substrate 102 may possess a thickness in range of approximately 500 um. A layer 105 can also be located between the substrate 102 and the sensing layer 104. Such a layer can be configured from a material such as, for example, Cr, and may possess a thickness in a range of 50-200 Angstroms, depending upon design considerations.

Figure 2:
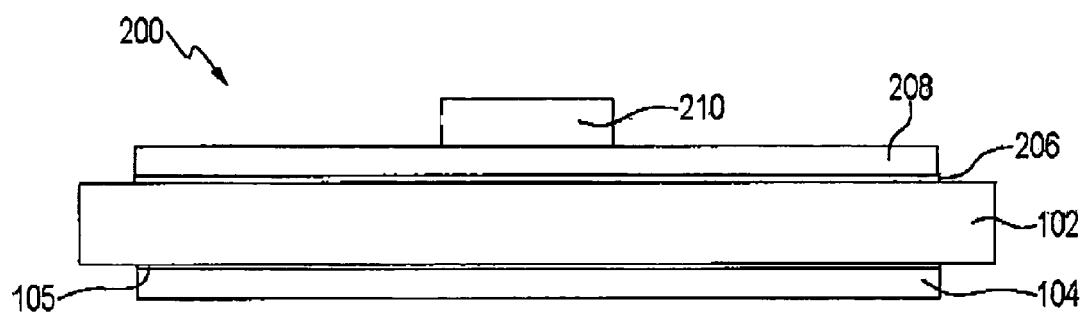
FIG. 2 illustrates a side view of an etch rate sensor system that can be implemented in accordance with an alternative embodiment.

FIG. 2 illustrates a side view of an etch rate sensor system 200 that can be implemented in accordance with an alternative embodiment. Note that in FIGS. 1-2, identical or similar parts or elements are generally indicated by identical reference numerals. Thus, system 200 includes substrate 102, and layers 104, 105. A sensing layer 208 is configured upon substrate 102 and above a layer 206 that is similar to layer 105. The layer 206 can be implemented, for example, as a layer of Cr material that is 50-200 Angstroms thick, depending upon design considerations. In the configuration depicted in FIG. 2 a large reactive electrode 210 is depicted configured upon the sensing layer 208. The configuration depicted in FIG. 2 differs from that of FIG. 1 in that a larger reactive electrode 210 is provided, whereas such a large reactive electrode is not required in the configuration depicted in FIG. 1. The configuration depicted in FIG. 1 therefore offers a preferred implementation.

System 200 can be thought of as constituting an oil quality sensing system composed of at least one acoustic wave viscosity sensing component, such as, for example, electrode 210, and an etch rate sensing component or etch rate sensing device comprising the piezoelectric substrate 102 and one or more sensing layers 208 configured upon said piezoelectric substrate 102. A gold layer (not shown in FIG. 2) can be configured above the sensing layer 208 and below the reactive electrode 210 depending upon design considerations. Such a gold layer can provide protection to the sensing layer 208, thereby extending the operating life of said oil quality sensing system 200. A sacrificial layer (not shown in FIG. 2) may be located between the piezoelectric substrate 102 and said gold layer in order permit a reaction to occur from a radial direction thereof.

One of the advantages of the design upon which system 100 and system 200 is based, is that such a design provides for a longer sensor life and a significantly higher Q value than is available with prior art devices. Prior etch rate or corrosivity sensors typically provide for a sensor configuration in which the entire electrode is exposed to the analytes. When acids attack the surface, the surface will become coarse, and this reduces the Q value significantly. When acids attack from the edge or "side" as illustrated, for example, by the curved arrows 109, 111 depicted in FIG. 1, the acids do not change the Q value that much. The life of the sensor system 100, 200 can be extended because the width/length/diameter is typically 10000 larger than the thickness of associated acoustic waves.

The configurations depicted in FIGS. 1-2 can be implemented in the context of an acoustic wave sensor. Thus, system 100 can function as an acoustic wave sensor, as well as system 200. Examples of acoustic wave sensors in which system 100 and/or 200 can be implemented include an acoustic plate mode sensor device (APM), a shear-horizontal surface acoustic wave sensor device (SH-SAW), and/or a bulk acoustic wave sensor device (BAW), a love wave sensor device, a surface transverse wave sensor device (STW), a shear-horizontal acoustic plate mode sensor device (SH-APM), a quartz crystal micro-balance (QCM) or a thickness-shear mode (TSM) sensor device, a flexural plate wave (FPW), surface-skimming bulk wave (SSBW), and/or a Lamb wave sensor device, again depending upon design considerations. Of course, sensor system 100 and/or 200 can be implemented in the context of a surface acoustic wave (SAW) sensor device.

It is contemplated that the use of the present invention can involve components having different characteristics. It is intended that the scope of the present invention be defined by the claims appended hereto, giving full cognizance to equivalents in all respects.

What is claimed is:

1. An oil quality sensing system, comprising:
an acoustic wave viscosity sensing component;
an etch rate sensing component comprising a piezoelectric substrate and at least one sensing layer configured upon said piezoelectric substrate, wherein said at least one sensing layer comprises at least one reactive electrode;
a gold layer configured above said at least one sensing layer such that acids are forced instead to attack said at least one reactive electrode from the side, wherein said gold layer provides protection to said at least one sensing layer, thereby extending an operating life of said oil quality sensing system;
a sacrificial layer located between said piezoelectric substrate and said gold layer in order permit a reaction to occur from a radial direction thereof.

2. The system of claim 1 wherein said at least one reactive electrode comprises an effective thickness that is approximately equivalent to a width or a length of said at least one reactive electrode, thereby extending said operation life of said etch rate sensor system.

3. The system of claim 1 wherein said oil quality sensing system is adapted for use in a permanent filter application.

4. The system or claim 1 wherein said at least one reactive electrode comprises a thickness of approximately 4000 Angstroms.

5. The system of claim 1 wherein said at least one reactive electrode comprises an electrode dimension in a range of approximately 4 mm to 6 mm.

6. The system or claim 1 wherein said at least one sensing layer is configured on a top side or said substrate.

7. An oil quality sensing system, comprising:
an acoustic wave viscosity sensing component;
an etch rate sensing component comprising a piezoelectric substrate and at least one sensing layer configured upon said plezoelectric substrate;
a gold layer configured above said at least one sensing layer such that acids are forced instead to attack said at least one reactive electrode from the side, wherein said gold layer provides protection to said at least one sensing layer, thereby extending an operating life of said oil quality sensing system; and
a sacrificial layer located between said plezoelectric substrate and said gold layer in order permit a reaction to occur from a radial direction thereof.

8. The system of claim 7 wherein said etch rate sensing component comprises a quartz crystal microbalance (QCM) electrode and said sacrificial layer forms a part of said QCM electrode.

9. The system of claim 7 wherein said etch rate sensing component comprises a bulk acoustic wave (BAW) electrode and said sacrificial layer forms a part of said BAW electrode.

10. The system of claim 7 wherein said etch rate sensing component comprises a shear horizontal surface acoustic wave (SH-SAW) electrode and said sacrificial layer forms a part of said SH-SAW electrode.

11. The system of claim 7 wherein said etch rate sensing component comprises an acoustic plate mode (APM) electrode and said sacrificial layer forms a part of said APM electrode.

12. The system of claim 7 wherein said etch rate sensing component comprises a Love wave electrode and said sacrificial layer forms a part of said Love wave electrode.

13. The system of claim 7 wherein said acoustic wave viscosity sensing component comprises at least one of the following: a quartz crystal microbalance (QCM) device, a Love wave sensor device, a shear horizontal surface acoustic wave (SH-SAW) sensor device, an acoustic plate mode (APM) sensor device, a shear horizontal acoustic plate mode (SH-APM) sensor device, or a flexural plate mode acoustic wave sensor device.

14. The system of claim 7, further comprising a reactive electrode configured above said gold layer.

15. A method for forming an oil quality sensor:
providing an acoustic wave viscosity sensing component;
providing an etch rate sensing component comprising a piezoelectric substrate and at least one sensing layer configured upon said piezoelectric substrate; said at least one sensing layer comprising at least one reactive electrode
configuring a gold layer configured above said at least one sensing layer such that acids are forced instead to attack said at least one reactive electrode from the side; and
configuring a sacrificial layer between said piezoelectric substrate and said gold layer in order to permit a reaction to occur from a radial direction thereof, wherein said gold layer provides protection to said at least one sensing layer, thereby extending an operating life of said oil quality sensing system.

16. The method of claim 15 wherein said at least one reactive electrode comprises an effective thickness that is approximately equivalent to a width or a length of said at leas one reactive electrode, thereby extending said operation life of said etch rate sensor system.

17. The method of claim 15 further comprising configuring said at least one sensing layer on a top side of said substrate.

18. The method of claim 15 wherein said at least one reactive electrode comprises a thickness of approximately 4000 Angstroms and an electrode size in a range of approximately 4 mm to 6 mm.

* * * * *